(12) United States Patent  (10) Patent No.: US 9,283,321 B2
Nelson et al.  (45) Date of Patent: Mar. 15, 2016

(54) SMART MEDICATION WASTE DISPOSAL

(75) Inventors: Elizabeth Nelson, Newton, MA (US);
Bart D. Peterson, Farmington, UT (US);
William R. Marshall, Sandy, UT (US);
Bryan G. Davis, Sandy, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 787 days.

(21) Appl. No.: 13/410,083

(22) Filed: Mar. 1, 2012

(65) Prior Publication Data

US 2012/0226447 A1 Sep. 6, 2012

Related U.S. Application Data

(60) Provisional application No. 61/450,198, filed on Mar. 8, 2011, provisional application No. 61/449,314, filed on Mar. 4, 2011, provisional application No. 61/450,204, filed on Mar. 8, 2011, provisional application No. 61/449,263, filed on Mar. 4, 2011.

(51) Int. Cl.
*G06F 19/00* (2011.01)
*A61M 5/168* (2006.01)

(52) U.S. Cl.
CPC ............... *A61M 5/168* (2013.01); *G06F 19/34* (2013.01); *G06F 19/3468* (2013.01)

(58) Field of Classification Search
USPC .......................................................... 702/25
See application file for complete search history.

(56) References Cited

U.S. PATENT DOCUMENTS

| | | |
|---|---|---|
| 3,631,437 A | 12/1971 | Campbell |
| 4,607,671 A | 8/1986 | Aalto et al. |
| 4,759,756 A | 7/1988 | Forman et al. |
| 4,846,005 A | 7/1989 | Bacehowski et al. |
| 5,046,496 A | 9/1991 | Betts et al. |
| 5,145,565 A | 9/1992 | Kater et al. |
| 5,301,543 A | 4/1994 | Reichert |
| 5,390,671 A | 2/1995 | Lord et al. |
| 5,563,584 A | 10/1996 | Rader et al. |
| 5,620,008 A | 4/1997 | Shinar et al. |
| 6,193,675 B1 | 2/2001 | Kraus et al. |
| 6,264,611 B1 | 7/2001 | Ishikawa et al. |
| 6,753,186 B2 | 6/2004 | Moskoff |
| 6,758,835 B2 | 7/2004 | Close et al. |
| 7,533,028 B2 * | 5/2009 | Mallett et al. ................ 705/308 |
| 7,811,279 B2 | 10/2010 | John |
| 8,287,073 B2 | 10/2012 | Schippers |
| 9,067,014 B2 * | 6/2015 | Nelson et al. |
| 9,155,833 B2 * | 10/2015 | Nelson et al. |
| 2003/0100861 A1 | 5/2003 | Bergeron et al. |

(Continued)

FOREIGN PATENT DOCUMENTS

EP 1 739 585 A2 1/2007
WO WO 02/096781 A1 12/2002

(Continued)

*Primary Examiner* — Huan Tran
(74) *Attorney, Agent, or Firm* — Jeanne Lukasavage; Craig Metcalf; Kirton McConkie

(57) ABSTRACT

A system for recording the wasting of fluids includes a waste disposal unit and a sensor system, having a sensor. The sensor can have one or more sensor elements in fluid communication with a fluid as it is wasted from a container into the waste disposal unit. The sensor system is configured to identify one or more drugs within the fluid and record the identity of the one or more drugs in a computer-readable medium electrically coupled to the sensor system.

16 Claims, 8 Drawing Sheets

(56) References Cited

U.S. PATENT DOCUMENTS

| | | | |
|---|---|---|---|
| 2004/0171983 A1 | 9/2004 | Sparks et al. | |
| 2006/0253297 A1* | 11/2006 | Mallett et al. | 705/1 |
| 2007/0100518 A1* | 5/2007 | Cooper | 701/29 |
| 2007/0135779 A1* | 6/2007 | Lalomia et al. | 604/319 |
| 2007/0179448 A1 | 8/2007 | Lim et al. | |
| 2007/0191700 A1 | 8/2007 | Say et al. | |
| 2008/0129475 A1 | 6/2008 | Breed et al. | |
| 2008/0169044 A1 | 7/2008 | Osborne et al. | |
| 2008/0237092 A1 | 10/2008 | Mallett et al. | |
| 2008/0319795 A1* | 12/2008 | Poteet et al. | 705/3 |
| 2009/0036764 A1 | 2/2009 | Rivas et al. | |
| 2009/0216205 A1* | 8/2009 | Ryan et al. | 604/319 |
| 2009/0275815 A1 | 11/2009 | Bickoff et al. | |
| 2010/0145274 A1 | 6/2010 | Royce | |
| 2010/0191084 A1 | 7/2010 | Shah et al. | |
| 2010/0280486 A1 | 11/2010 | Khair et al. | |
| 2010/0305499 A1 | 12/2010 | Matsiev et al. | |
| 2011/0009817 A1 | 1/2011 | Bennett et al. | |
| 2011/0015583 A1 | 1/2011 | Davis et al. | |
| 2011/0060198 A1 | 3/2011 | Bennett et al. | |
| 2011/0060229 A1 | 3/2011 | Hulvershorn et al. | |
| 2011/0112474 A1 | 5/2011 | Bochenko et al. | |
| 2011/0144530 A1 | 6/2011 | Felder | |
| 2011/0264069 A1 | 10/2011 | Bochenko | |
| 2011/0270027 A1 | 11/2011 | Augarten et al. | |
| 2012/0016345 A1 | 1/2012 | Carter et al. | |
| 2012/0065617 A1 | 3/2012 | Matsiev et al. | |
| 2012/0222468 A1* | 9/2012 | Nelson et al. | 73/61.41 |
| 2013/0177455 A1 | 7/2013 | Kamen et al. | |
| 2013/0226137 A1 | 8/2013 | Brown | |

FOREIGN PATENT DOCUMENTS

| | | | |
|---|---|---|---|
| WO | WO 2004/033003 A1 | 4/2004 | |
| WO | WO 2004/095379 A1 | 11/2004 | |
| WO | WO 2009/114115 * | 9/2009 | A61M 5/168 |
| WO | WO 2009/114115 A1 | 9/2009 | |

* cited by examiner

SMART MEDICATION WASTE DISPOSAL

RELATED APPLICATIONS

This application claims the benefit of U.S. Provisional Application No. 61/450,198 filed Mar. 8, 2011, entitled SMART WASTE DISPOSAL, U.S. Provisional Application No. 61/449,314 filed Mar. 4, 2011, entitled SMART DELIVERY CONTAINER, U.S. Provisional Application No. 61/450,204 filed Mar. 8, 2011, entitled SMART DRUG CONTAINER ATTACHMENT, and U.S. Provisional Application No. 61/449,263 filed Mar. 4, 2011, entitled SMART CLOSED LOOP MEDICATION ADMINISTRATION, each of which is incorporated herein by reference in their entirety. which is incorporated herein by reference.

BACKGROUND OF THE INVENTION

There is a significant concern around narcotic diversions and drug abuse within hospitals; the use of narcotics is especially an area of focus. In an effort to avoid drug diversions, some hospitals and other care facilities have protocols in place that require one person to waste the narcotic (such as into a sink or a container) while another person observes the wasting to ensure the narcotic was properly wasted. There are inherent problems with this method. For example, the drug could be substituted prior to wasting without the observer knowing. Alternatively, the waster and observer could be diverting the drug together or the observer could ignore the drug diversion for professional or personal reasons. In addition, the observer spends valuable time monitoring the disposal process instead of focusing on patient care.

Alternatively, some drugs are not required to be wasted if the drug can be re-dispensed to another patient. In these cases, the drug can be sent back to the pharmacy where it is re-dispensed. However, in this circumstance, the pharmacist must rely on the chain of control and trust that the returned drug is indeed the drug identified on the container's label. If the drug has been diverted, a patient will not receive the needed medication.

Thus, while techniques and systems are available for use in preventing narcotic diversions and drug abuse, challenges still exist. Accordingly, it would be an improvement in the art to augment or even replace current techniques with other techniques.

SUMMARY OF THE INVENTION

The present invention allows for the proper identification of wasted fluids to verify that unused fluids are not stolen, replaced, diverted or illegally used. Thus, a fluid tracking system and method is provided which enables the identification of a fluid and its volume at the point of wasting or re-dispensing. The fluid tracking may also determine whether the identity and volume of the wasted fluid are the same as that which should remain after the fluid has been used on a patient.

In some implementations, a fluid tracking system comprises a waste disposal unit having a sensor for detecting a characteristic of a fluid. The fluid tracking system further comprises a processor unit operably coupled to the sensor and configured to receive and record the characteristic of the fluid. The sensor is positioned on or near a port of the waste disposal unit, wherein the port is configured to receive a container having a fluid for wasting. The sensor is generally positioned within a fluid pathway of the port such that as the fluid is wasted, the sensor directly contacts the fluid. As the fluid is wasted, the sensor tests the fluid to identify one or more characteristics of the fluid. The characteristics of the fluid can include an identity of the fluid, an identity of one or more constituents within the fluid, a concentration of a constituent within the fluid, a dose of a constituent within the fluid, a degradation (e.g., expiration or contamination) of the fluid, a volume of the fluid, a diluent of the fluid, and a temperature of the fluid.

Some implementations of the present invention further include a fluid tracking system which is configured to record and identify characteristic of a fluid in a computer-readable medium or electronic record, such as an electronic medical record (EMR) or a Pharmacy Information System. For example, the fluid tracking system may record the identity of the one or more drugs within the wasted fluid, a date and time of the wasting, an identity of the individual wasting the fluid, and other such information as may be useful for internal care center inventory. The recorded characteristics or information may be used for record-keeping purposes, patient billing purposes, inventory analysis purposes, identifying drug diversion and identifying unnecessary waste of drugs (or drug usage efficiency). For example, in some implementations a sensor of the fluid tracking system is able to detect a discrepancy in one or more characteristic of the wasted fluid. Where a discrepancy is detected, the fluid tracking system may provide an alert. In some instances, a fluid tracking system tracks and records a frequency and volume of a specific wasted fluid. This information is then made available to a pharmacy to assist the pharmacy in managing the inventory of the specific wasted fluid. In some configurations, the fluid tracking system may further record information on an electronic medication record system. The electronic medical record system may then create a log or record of fluid wasting generally, or create a record of wasting for a specific fluid prepared for a particular patient.

The fluid tracking system in accordance with the present invention may include various inputs configured to receive information about the waster's identity, the fluid characteristics, the fluid's history, and the like. For instance, in some embodiments a fluid tracking system is provided having an input for reading a machine recognizable code attached to a container as a label, wherein the machine recognizable code contains information regarding an initial identity or characteristic of a fluid contained therein. In other embodiments, a user enters or otherwise provides information into a fluid tracking system, wherein the information relates to an initial identity or characteristic of a fluid being wasted. Other inputs are provided for accessing information from the EMR system, wherein the information from the EMR system comprises information regarding an initial desired identity of a wasted fluid and an expected volume of a wasted fluid. The fluid tracking system may further compare and verify the information obtained from the EMR system to the information detected by a sensor of the fluid tracking system. In this way, the fluid tracking system may detect a discrepancy which may indicate that a fluid was diverted.

These and other features and advantages of the present invention may be incorporated into certain embodiments of the invention and will become more fully apparent from the following description and appended claims, or may be learned by the practice of the invention as set forth hereinafter. The present invention does not require that all the advantageous features and all the advantages described herein be incorporated into every embodiment of the invention.

BRIEF DESCRIPTION OF THE SEVERAL VIEWS OF THE DRAWINGS

In order that the manner in which the above-recited and other features and advantages of the invention are obtained will be readily understood, a more particular description of the invention briefly described above will be rendered by reference to specific embodiments thereof which are illustrated in the appended drawings. These drawings depict only typical embodiments of the invention and are not therefore to be considered as limiting the scope of the invention.

DETAILED DESCRIPTION OF THE INVENTION

Figure 1:
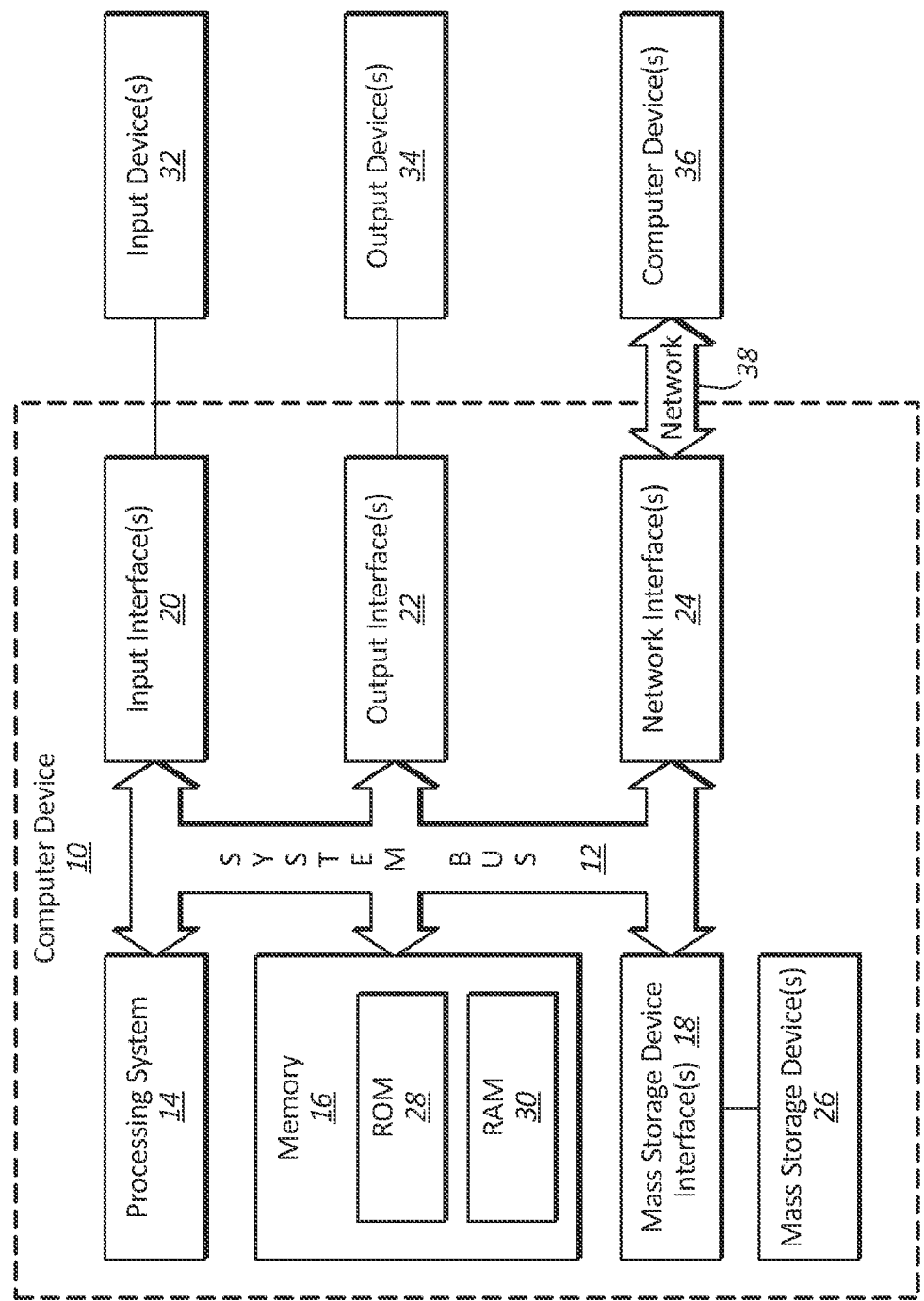
FIG. 1 shows a representative computer system suitable for use with embodiments of the present invention.

A description of embodiments of the present invention will now be given with reference to the Figures. It is expected that the present invention may take many other forms and shapes, hence the following disclosure is intended to be illustrative and not limiting, and the scope of the invention should be determined by reference to the appended claims.

Embodiments of the invention address the problem of tracking fluids, such as medicaments, used in acute care facilities. Thus, embodiments of the present invention provide systems, methods, and computer-readable media storing computer instructions for implementing methods for tracking and reporting the wasting of fluids.

For convenience, the word "fluid" is used herein to refer to a liquid medicament or other liquid solution for which tracking is desirable in an acute care facility. This word, "fluid," is not intended to be limited to any drug type or classification, but is merely a word choice of convenience, and should be understood to apply to any type of fluid for which a tracking in accordance with the principles described herein. Therefore, unless the specific use of the word "fluid" herein is specific to a drug type or classification, the word should be read broadly as described.

Similarly, the word "sensor" is used herein to refer to any device that measures a physical quantity and converts it into a signal which can be read by an observer or by an instrument. This word, "sensor," is not intended to be limited to any specific type of technology or physical properties, but is merely a word choice of convenience, and should be understood to apply to any type of sensor which is compatible with the principles described herein. Therefore, unless the specific use of the word "sensor" herein is specific to a type of technology or physical property, the word should be read broadly as described.

In some embodiments, a fluid identification system is provided which identifies and tracks the disposal of a fluid. In some instances, the fluid identification system comprises a single sensor associated with a device or container in which the fluid is stored or through which the fluid passes. For example, in some embodiments a fluid identification system is provided comprising a single sensor associated with an IV bag. In other embodiments, a fluid identification system is provided comprising a single sensor associated with a syringe. Further still, in some instances a fluid identification system is provided comprising a single sensor associated with at least one of an ampoule, a vial, and a disposal system used with the fluid.

A fluid identification system in accordance with the present invention may further include a plurality of sensors. Further, the plurality of sensors may be operably connected to a computer system or computer device having a computer-readable media for implementing methods for tracking and reporting the wasting of a fluid. Accordingly, the fluid identification system may be used to track and verify the proper disposal or wasting of the fluid.

FIG. 1 and the corresponding discussion are intended to provide a general description of a suitable operating environment in which embodiments of the invention may be implemented. One skilled in the art will appreciate that embodiments of the invention may be practiced by one or more computing devices and in a variety of system configurations, including in a networked configuration. However, while the methods and processes of the present invention have proven to be particularly useful in association with a system comprising a general purpose computer, embodiments of the present invention include utilization of the methods and processes in a variety of environments, including embedded systems with general purpose processor units, digital/media signal processors (DSP/MSP), application specific integrated circuits (ASIC), stand alone electronic devices, and other such electronic environments.

Embodiments of the present invention embrace one or more computer-readable media, wherein each medium may be configured to include or includes thereon data or computer executable instructions for manipulating data. The computer executable instructions include data structures, objects, programs, routines, or other program modules that may be accessed by a processing system, such as one associated with a general-purpose computer capable of performing various different functions or one associated with a special-purpose computer capable of performing a limited number of functions. Computer executable instructions cause the processing system to perform a particular function or group of functions and are examples of program code means for implementing steps for methods disclosed herein. Furthermore, a particular sequence of the executable instructions provides an example of corresponding acts that may be used to implement such steps. Examples of computer-readable media include random-access memory ("RAM"), read-only memory ("ROM"), programmable read-only memory ("PROM"), erasable programmable read-only memory ("EPROM"), electrically erasable programmable read-only memory ("EEPROM"), compact disk read-only memory ("CD-ROM"), or any other device or component that is capable of providing data or executable instructions that may be accessed by a processing system. While embodiments of the invention embrace the use of all types of computer-readable media, certain embodiments as recited in the claims may be limited to the use of tangible, non-transitory computer-readable media, and the phrases "tangible computer-readable medium" and "non-transitory computer-readable medium" (or plural variations) used herein are intended to exclude transitory propagating signals per se.

With reference to FIG. 1, a representative system for implementing embodiments of the invention includes computer device 10, which may be a general-purpose or special-purpose computer or any of a variety of consumer electronic devices. For example, computer device 10 may be a personal computer, a notebook computer, a netbook, a tablet computer such as the iPad® manufactured by Apple or any of a variety of Andriod™-based tablet computers produced by multiple manufacturers, a personal digital assistant ("PDA") or other hand-held device, a workstation, a minicomputer, a mainframe, a supercomputer, a multi-processor system, a network computer, a processor-based consumer electronic device, or the like.

Computer device 10 includes system bus 12, which may be configured to connect various components thereof and enables data to be exchanged between two or more components. System bus 12 may include one of a variety of bus structures including a memory bus or memory controller, a peripheral bus, or a local bus that uses any of a variety of bus architectures. Typical components connected by system bus 12 include processing system 14 and memory 16. Other components may include one or more mass storage device interfaces 18, input interfaces 20, output interfaces 22, and/or network interfaces 24, each of which will be discussed below.

Processing system 14 includes one or more processors, such as a central processor and optionally one or more other processors designed to perform a particular function or task. It is typically processing system 14 that executes the instructions provided on computer-readable media, such as on memory 16, a solid-state drive, a flash drive, a magnetic hard disk, a removable magnetic disk, a magnetic cassette, an optical disk, or from a communication connection, which may also be viewed as a computer-readable medium.

Memory 16 includes one or more computer-readable media that may be configured to include or includes thereon data or instructions for manipulating data, and may be accessed by processing system 14 through system bus 12. Memory 16 may include, for example, ROM 28, used to permanently store information, and/or RAM 30, used to temporarily store information. ROM 28 may include a basic input/output system ("BIOS") having one or more routines that are used to establish communication, such as during start-up of computer device 10. RAM 30 may include one or more program modules, such as one or more operating systems, application programs, and/or program data.

One or more mass storage device interfaces 18 may be used to connect one or more mass storage devices 26 to system bus 12. The mass storage devices 26 may be incorporated into or may be peripheral to computer device 10 and allow computer device 10 to retain large amounts of data. Optionally, one or more of the mass storage devices 26 may be removable from computer device 10. Examples of mass storage devices include solid-state drives, flash drives, hard disk drives, magnetic disk drives, tape drives and optical disk drives. A mass storage device 26 may read from and/or write to a magnetic hard disk, a removable magnetic disk, a magnetic cassette, an optical disk, or another computer-readable medium. Mass storage devices 26 and their corresponding computer-readable media provide nonvolatile storage of data and/or executable instructions that may include one or more program modules such as an operating system, one or more application programs, other program modules, or program data. Such executable instructions are examples of program code means for implementing steps for methods disclosed herein.

One or more input interfaces 20 may be employed to enable a user to enter data and/or instructions to computer device 10 through one or more corresponding input devices 32. Examples of such input devices include a keyboard and alternate input devices, such as a mouse, trackball, touch screen, light pen, stylus, or other pointing device, a microphone, a joystick, a game pad, a satellite dish, a scanner, a camcorder, a digital camera, and the like. Similarly, examples of input interfaces 20 that may be used to connect the input devices 32 to the system bus 12 include a serial port, a parallel port, a game port, a universal serial bus ("USB"), an integrated circuit, a firewire® (IEEE 1394), or another interface. For example, in some embodiments input interface 20 includes an application specific integrated circuit (ASIC) that is designed for a particular application. In a further embodiment, the ASIC is embedded and connects existing circuit building blocks.

One or more output interfaces 22 may be employed to connect one or more corresponding output devices 34 to system bus 12. Examples of output devices include a monitor or display screen or other electronic display, a speaker, a printer, a multi-functional peripheral, and the like. A particular output device 34 may be integrated with or peripheral to computer device 10. Examples of output interfaces include a video adapter, an audio adapter, a parallel port, and the like. Examples of electronic displays include monitors, televisions, e-ink displays, projection displays, or any other display capable of displaying changing information under the control of a computer device.

One or more network interfaces 24 enable computer device 10 to exchange information with one or more other local or remote computer devices, illustrated as computer devices 36, via a network 38 that may include hardwired and/or wireless links. Examples of network interfaces include a network adapter for connection to a local area network ("LAN") or a modem, wireless link, or other adapter for connection to a wide area network ("WAN"), such as the Internet. The network interface 24 may be incorporated with or peripheral to computer device 10. In a networked system, accessible program modules or portions thereof may be stored in a remote memory storage device. Furthermore, in a networked system computer device 10 may participate in a distributed computing environment, such as a cloud-based computer environment, where functions or tasks are performed by a plurality of networked computer devices.

Figure 2:
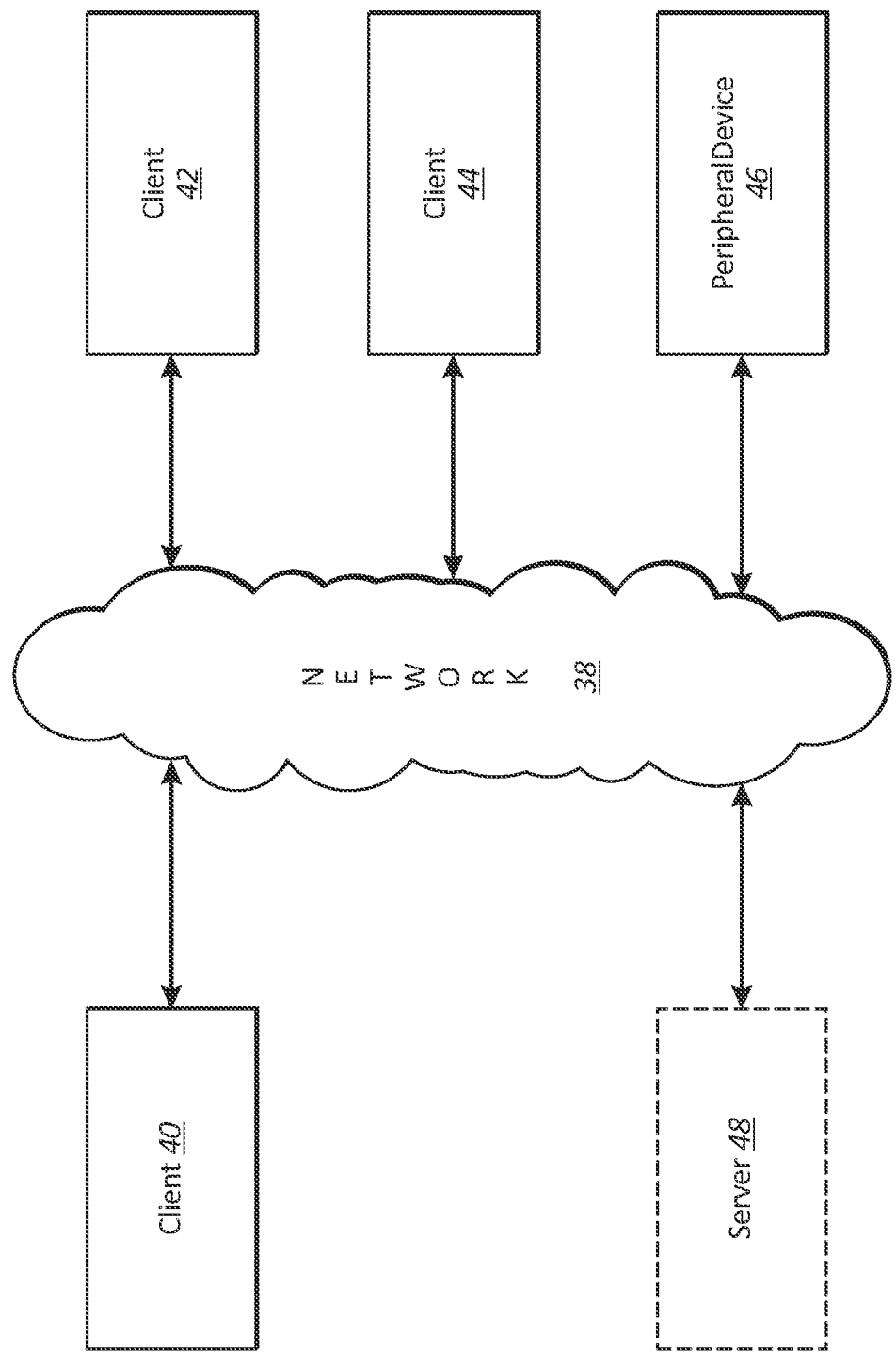
FIG. 2 shows a representative networked computer system suitable for use with embodiments of the present invention.

Thus, while those skilled in the art will appreciate that embodiments of the present invention may be practiced in a variety of different environments with many types of system configurations, FIG. 2 provides a representative networked system configuration that may be used in association with embodiments of the present invention. The representative system of FIG. 2 includes a computer device, illustrated as client 40, which is connected to one or more other computer devices (illustrated as client 42 and client 44) and one or more peripheral devices (illustrated as multifunctional peripheral (MFP) MFP 46) across network 38. While FIG. 2 illustrates an embodiment that includes a client 40, two additional clients, client 42 and client 44, one peripheral device, MFP 46, and optionally a server 48, which may be a print server, connected to network 38, alternative embodiments include more or fewer clients, more than one peripheral device, no peripheral devices, no server 48, and/or more than one server 48 connected to network 38. Other embodiments of the present invention include local, networked, or peer-to-peer environments where one or more computer devices may be connected to one or more local or remote peripheral devices. Moreover, embodiments in accordance with the present invention also embrace a single electronic consumer device, wireless networked environments, and/or wide area networked environments, such as the Internet.

Similarly, embodiments of the invention embrace cloud-based architectures where one or more computer functions are performed by remote computer systems and devices at the request of a local computer device. Thus, returning to FIG. 2, the client 40 may be a computer device having a limited set of hardware and/or software resources. Because the client 40 is connected to the network 38, it may be able to access hardware and/or software resources provided across the network 38 by other computer devices and resources, such as client 42, client 44, server 48, or any other resources. The client 40 may access these resources through an access program, such as a web browser, and the results of any computer functions or resources may be delivered through the access program to the user of the client 40. In such configurations, the client 40 may be any type of computer device or electronic device discussed above or known to the world of cloud computing, including traditional desktop and laptop computers, smart phones and other smart devices, tablet computers, or any other device able to provide access to remote computing resources through an access program such as a browser.

Referring generally to FIGS. 3-8, various representative embodiments of a fluid tracking system and methods to monitor and track the disposal of intravenous (IV) fluids, subcutaneous and intramuscular injectable fluids and liquid oral medications (herein referred to simply as fluids or IV fluids) is shown. In general, fluid tracking systems of the present invention comprise sensors configured to detect various characteristics, parameters, constituents and other identifying properties of fluids being wasted following use.

Figure 3:
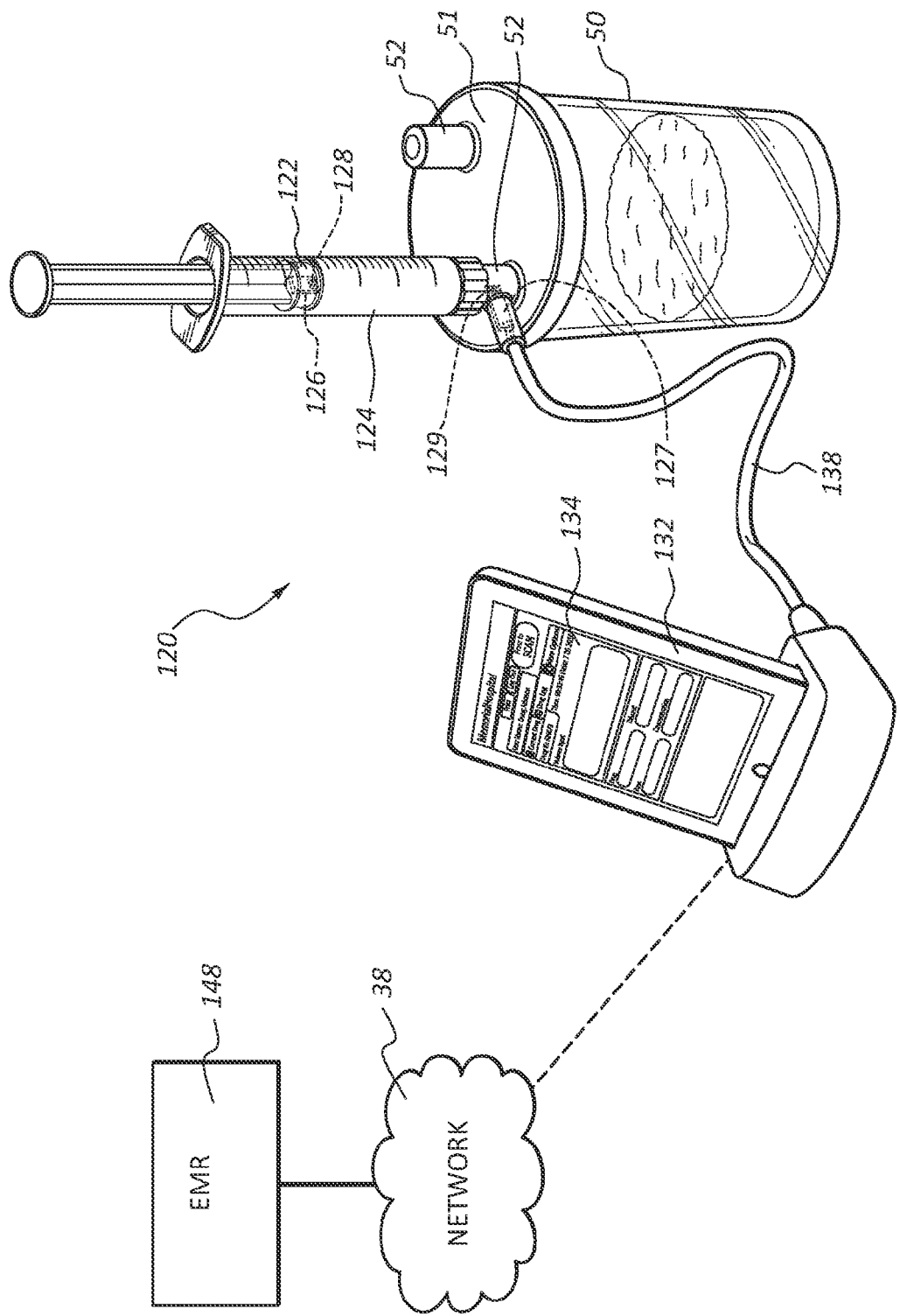
FIG. 3 illustrates a perspective view of a waste disposal system operably connected to an electronic recordable medium in accordance with a representative embodiment of the present invention.

Referring now to FIG. 3, a representative fluid tracking system 120 is shown. In some embodiments, a fluid tracking system 120 is provided or established within a single care facility, such as a hospital, or may be used in a group of various related facilities, such as an off-site pharmacy, a remote doctor's office, and a hospital (or other care facility) to monitor or track the disposal of various fluids. A fluid tracking system 120 that is linked with a group of various related facilities is beneficial for situations where an ordered drug is returned to the pharmacy to be wasted rather than the nurse or physician wasting the remaining drug following administration of the drug to a patient. Thus, fluid tracking system 120 is able to track the drug across multiple facilities and maintain accurate records for pharmaceutical efficiency, inventory and/or auditing purposes.

In hospitals and other care facilities, a common practice is for a physician to prescribe a fluid to a patient. In some embodiments, the fluid is administered to the patient intravenously. Some fluids comprise one or more constituents which are determined to diagnosis, cure, mitigate, treat, or prevent a disease or other illness. In some embodiments, a desired drug is compounded into an IV fluid by combining the drug with a diluent. Once compounded, the fluid is placed into a container 122, such as a syringe, and IV bag, an ampoule, a vial, an auto-injector container, or another such container which is needed to administer the fluid to a patient. Following administration of the fluid to the patient, any excess quantities of the fluid must be wasted or otherwise disposed or re-dispensed by the caregiver.

In some embodiments, container 122 comprises a sensor 126 which is configured to identify at least one of an identity, a characteristic, a constituent, a diluent, a perimeter and/or a characteristic of a fluid 124 stored in container 122. In some embodiments, sensor 126 is configured to perform one or more tests on the fluid 124 as it is wasted into a waste disposal unit 50. Sensor 126 is generally positioned in proximity to fluid 124 such that a sensor element 128 of sensor 126 is in contact with fluid 124. For example, in some embodiments sensor 126 is at least partially embedded within a plunger component of a syringe 122 such that sensor element 128 is exposed to fluid 124. More specifically, sensor 126 and sensor element 128 may be embedded into a stopper portion of the syringe's plunger. In other embodiments, sensor 126 is embedded with another portion of the syringe 122, such as the inner surface or a distal spout of syringe 122.

Sensor 126 may include any technology, structure or property capable of detecting a desired parameter or characteristic of fluid 124. In some embodiments, a waste disposal unit and/or a fluid container is provided having a sensor as disclosed in International Application Number WO 2009/114115, published Sep. 17, 2009, which is incorporated herein by reference. Examples of ways in which a sensor is coupled to a container are described and shown in U.S. patent application Ser. No. 13/185,146, filed Jul. 18, 2011, titled SYSTEM OF IDENTIFYING DRUGS WITHIN A CONTAINER OF FLUID, which is incorporated herein by reference in its entirety.

In some instances, the wasting fluid is monitored using a fluid tracking system 120. In some embodiments, fluid tracking system 120 comprises a waste disposal unit 50 operably connected to a processor unit 132. Fluid tracking system 120 may further include an electronic record, such as an electronic medical record (EMR) 148 operably connected to processor unit 132 via a network 38. When information is acquired by processor unit 132 from waste disposal unit 50, the information is transmitted to EMR 148 where the information is made accessible to other caregivers.

EMR 148 generally comprises a computerized medical record for a patient, as known in the art. In some embodiments, EMR 148 is configured to receive and store information relating to a fluid detected and tracked by fluid tracking system 120. EMR 148 may further include general information relating to the treatment of the patient, such as the patient's medical history, patient contact information, and patient insurance and billing information. In some embodiments, the EMR 148 further comprises an electronic medication administration record (EMAR) which includes specific information relating to the administration of medications to a patient. Accordingly, in some embodiments information relating to a fluid detected and tracked by fluid tracking system 120 is integrated into the EMAR of EMR 148. Further, information stored in the EMAR may be accessible to fluid tracking system 120, thereby enhancing the detection and tracking capabilities of fluid tracking system 120.

Network 38 may include a server on which a computer executable program is loaded having instructions for receiving, analyzing, and storing information received from waste disposal unit 50 and processor unit 132. Network 38 may further include network security software or other precautionary software as may be required to comply with Health Information Patient Privacy Act requirements. In some embodiments, network 38 comprises a local area network. In other embodiments, network 38 is a global area network.

Processor unit 132 generally includes a computer system in which some or all of the processing logic can be implemented for identifying the contents and characteristics of a fluid. Processor unit 132 may further be incorporated or integrated into another device or computer system. For example, processor unit 132 may be incorporated into an infusion or syringe pump, an automated dispensing cabinet (ADC), a bedside computer system, a patient monitor, or other suitable computer system or fluid-interacting device.

In some embodiments, processor unit 132 further comprises computer-executable instructions configured to cause the processor to execute functions for implementing logical operations. For example, in some embodiments computer-executable instructions are provided to implement a process for processing, storing, displaying or transmitting data relating to the identity of one or more components of a fluid.

In some embodiments, processor unit 132 further comprises an integrated display device 134. In other embodiments, processor unit 132 is operably coupled to a separate display device (not shown). Display device 134 may include any variety of display devices, such as a liquid crystal display (LCD) device, a cathode ray tube (CRT) display device, plasma display panel (PDP), light emitting diode (LED) display, or other such display devices known in the art. In some embodiments, display device 134 is a bedside display located at the point of care of a patient. Such bedside displays are commonly located in hospitals and other care facilities. As such, display device 134 is positioned in close proximity to the patient. In some embodiments, a display device 134 is connected to an IV pole or wall within a patient's room. Display device 134 is further coupled to processor unit 132 and/or an information technology infrastructure of a care facility.

Some embodiments, display device 134 displays information related to the identity of a fluid detected by a waste disposal unit 50 of fluid tracking system 120. Display device 134 may further display patient information, medication administration history, information regarding the safety status of a drug, information regarding the status of proper administration of the fluid, information regarding alerts or warnings related to the administration of a fluid to a patient, date, time, location, and other patient-related, facility-related, or treatment-related information.

In some embodiments, processor unit 132 further comprises a graphical user interface (GUI) 134 that displays the identity of a fluid. GUI 134 may be configured to display any information which may be desired in treating a patient. In some embodiments, GUI 134 further comprises a touch-screen display having input regions wherein a user can input data relating to the treatment of a patient. Processor unit 132 may further include a push button or other means whereby a user can initiate a scan to detect a fluid being wasted.

In some embodiments, waste disposal unit 50 comprises a receptacle having a lid 51 including one or more ports 52 configured to receive container 122 holding liquid 124 for disposal. In some embodiments, a first port 52 is provided to receive a first type of container 122, and a second port 52 is provided to receive a second type of container. In other embodiments, lid 51 comprises a plurality of ports having a variety of interfaces for receiving various types of containers.

Figure 4:
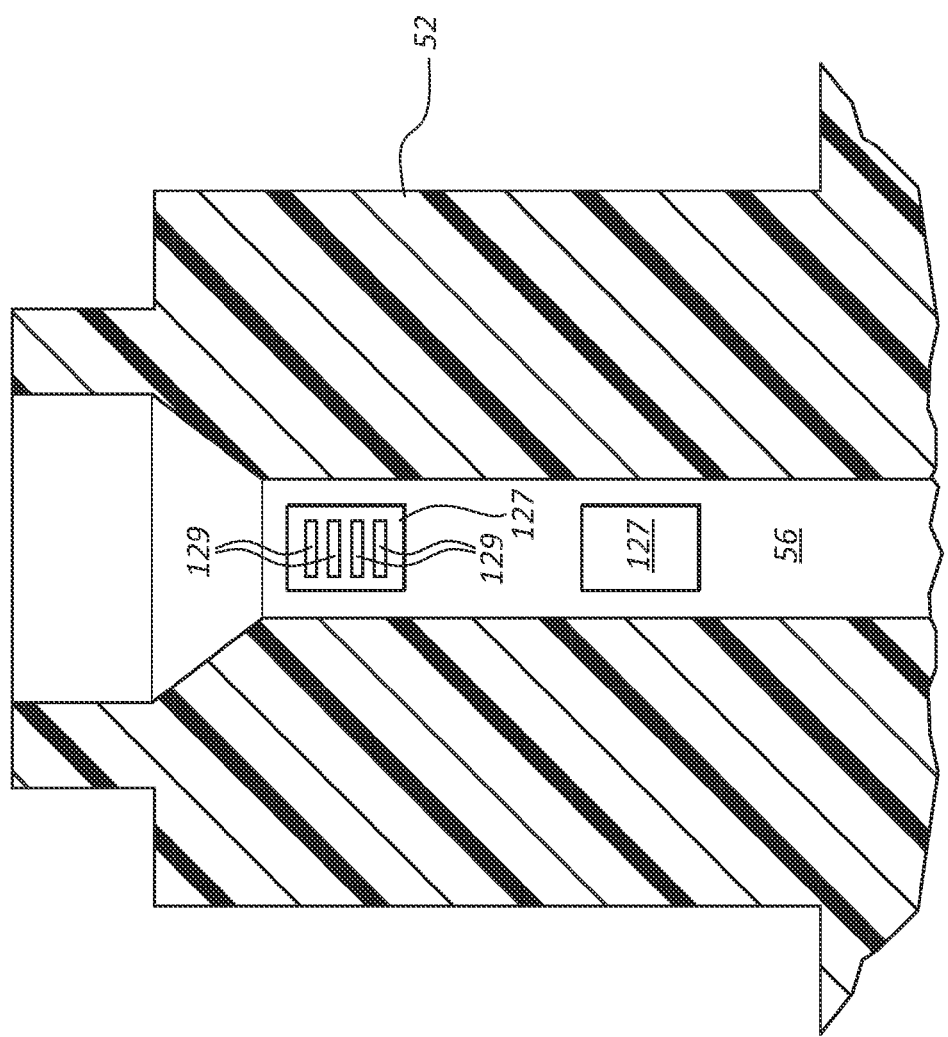
FIG. 4 illustrates a cross section view of a port of a waste disposal unit in accordance with a representative embodiment of the present invention.

Disposal unit 50 further comprises a sensor 127 coupled to a portion of port 52 and in a fluid pathway of disposal unit 50. In some embodiments, sensor 127 is positioned within port 52 so as to be in a fluid pathway 56 of port 52, as shown in FIG. 4. As such, fluid being wasted from container 122 into disposal unit 50 flows over sensor 127 thereby providing sensing measurements to processor unit 132. In some embodiments, sensor 127 further comprises a sensor element 129 which is configured to detect a specific characteristic or parameter of fluid 124 as it is being wasted into disposal unit 50.

Sensor elements 128 and 129 are generally positioned such that a sensing surface of the sensor elements interacts with the fluid of interest. In some embodiments, the sensor element comprises an electrode. In other embodiments, the sensor comprises a semiconductor device mounted on a printed circuit board or other substrate. Further still, in some embodiments the sensor and sensor element are powered and driven with dedicated electronics or an external power source, such as a battery.

Sensors 126 and 127 may be configured to sense or detect any characteristic of a desired fluid. In some embodiments, sensor 126 is configured to sense the impedance of a fluid. For example, an electrical signal may be driven through the sensor elements 128 of sensor 126 into the fluid at a range of frequencies. Sensor elements 128 and 129 may then measure the current generated in the fluid. The measured current may then be conditioned or processed by at least one of the sensor and the operably connected processor unit 132. Data received or sensed by the sensors may further be used to form frequency dependent maps of the impedance or admittance of the fluid. The maps, or fluid signatures, may be unique to each fluid of interest, its concentration, its component, its purity and its state of degradation. In some embodiments, processor unit 132 compares the fluid signature of a wasted fluid to a library of preloaded fluid signatures to aid in identifying the fluid or a characteristic of the fluid. In some configurations, the sensors utilize one or more alternative or additional sensing methods to sense one or more parameters or characteristics of fluid 124.

For example, in some embodiments processor unit 132 receives raw data from sensor elements 128 and 129. Processor unit 132 processes the raw data to determine a characteristic of the fluid. Processor unit 132 then analyzes the identified characteristic against a library of characteristics to determine a fit of the identified characteristic. Processor unit 132 then displays the results of the match. Processor unit 132 may further display other information, such as flow rate, volume, temperature, etc. as may be received from the sensors.

In some embodiments, a fluid tracking system 120 in accordance with the present invention uses a multi-parametric approach to identify the contents and characteristics of a fluid. In such an approach, multiple parameters (e.g. multiple fluid properties such as without limitation refractive index, electrochemical potential, impedance, admittance, conductivity, etc.) are sensed, and the combination of said sensed parameters are correlated to obtain a resolution of the various components within a fluid. For example, a fluid may be sensed with multiple sensors, or with a sensor having multiple sensor elements. A fluid may be further sensed via multiplexing a sensor element to obtain independent sensing measurements. Such multi-parametric approaches advantageously provide for improved resolution of components within a fluid being wasted.

Sensors 126 and 127 may be electronically coupled to the processor unit 132 via a communication link 138, through which the processor unit 132 electronically communicates with and/or electronically powers the sensors. For example, communication link 138 may include a wireless link (e.g., WiFi, Bluetooth®, WiMax, IR, RF, or other known wireless communication approaches), a direct wired connection (e.g. electrical wire or optical cable), or a direct connection via one or more direct lead contacts.

In some embodiments, the sensors are electronically powered via a separate power supply coupled to container 122 and/or disposal unit 50. For example, in some embodiments one or more power sources are coupled to container 122 and electronically coupled to sensor 126 to power sensor 126, such as a battery. In other embodiments, sensors 126 and/or 128 are powered wirelessly, such as via a wireless radio frequency technology. An example of a sensor powered with radio frequency technology is described in U.S. patent application Ser. No. 2008/0129475, which was published Jun. 5, 2008, and which is incorporated herein by reference in its entirety.

With continued reference to FIGS. 3 and 4, in some embodiments port 52 further comprises a plurality of sensors 127 and sensor elements 129 positioned in fluid pathway 56, wherein each sensor element 129 is configured to detect at least one characteristic or identity of fluid 124. Port 52 may further include an adapter (not shown) which is configured to compatibly receive a surface of container 122. For example, in some embodiments an adapter is provided which includes electrical contacts or other circuitry whereby to establish communication between a sensor 126 of container 122 and processor unit 132 via port 52 and communication link 138. As such, processor unit 132 may collect, compare and verify fluid data from sensors 126 and 127 to determine proper and complete disposal.

In some instances, fluid tracking system 120 accesses information stored in the patient's EMR 148 to assist in determining whether a portion of fluid 124 may have been diverted, illegally modified, or stolen. For instance, in some embodiments fluid tracking system 120 can verify whether the concentration of a constituent in the wasted fluid corresponds to what is recorded in the EMR 148.

As a non-limiting example, in one implementation an EMR 148 indicates that the container 122 originally included 10 mL of fluid 124, 5 mL of which was prescribed and administered to a patient. Based on this information, fluid tracking system 120 determines that 5 mL of fluid will be wasted from container 122. If less than 5 mL of fluid is wasted, an error code is generated on processor unit 132 thereby alerting the user of the deficiency.

By way of further non-limiting example, in some embodiments EMR 148 contains data regarding the original or expected drug concentration of a wasted fluid. Therefore, in the event that the fluid 124 has been diluted or otherwise tampered with, an error code is generated by processor unit 132 thereby alerting the user of the discrepancy.

Figure 5:
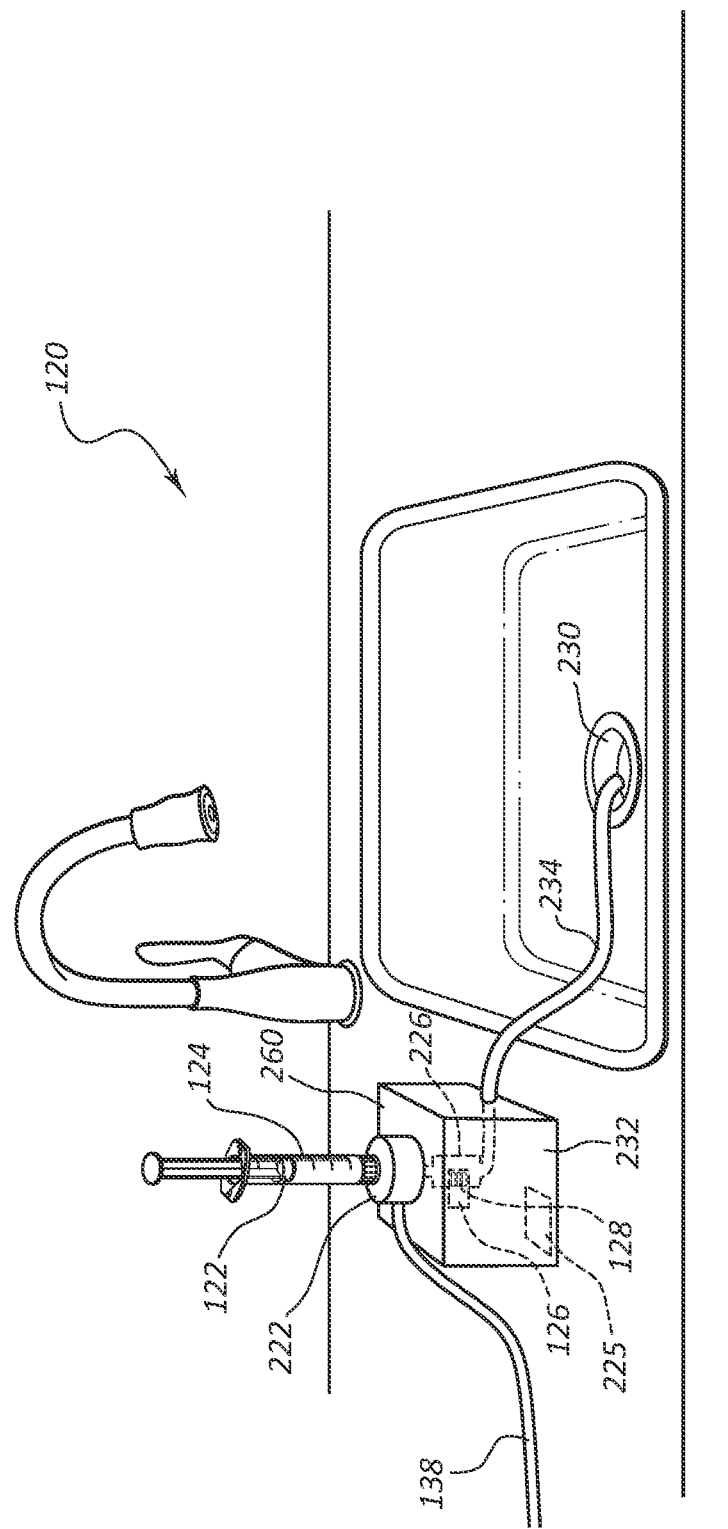
FIG. 5 illustrates a perspective view of a waste disposal system in accordance with a representative embodiment of the present invention.

Reference will now be made to FIG. 5, which illustrates another configuration of a waste disposal unit 260. Since some drugs are commonly wasted in a drain 230, a waste disposal unit 260 can lead fluids to a drain 230, while identifying the contents and characteristics of the fluid 124. Fluids may also be disposed into a chemical treatment system while identifying the contents and characteristics of the fluid 124. As shown, in some configurations a waste disposal unit 260 includes a housing 232 having a port 222. As a fluid 124 is introduced into the port 222, the fluid flows through a fluid path 226, which may include a tube 234 leading to a drain 230. A sensor 126 can be disposed within the housing 232 with one or more sensing elements 128 disposed within the fluid path 226. The one or more sensing elements 128 can be in fluid communication with fluid 124 as it is wasted. In this way, the wasted fluid can be identified and recorded.

Various hospital or other care facilities and/or governmental regulations require that records be kept of some or all fluids that are wasted. Accordingly, when fluid 124 is wasted via waste disposal unit 50 or 260, the fluid tracking system 120 can record one or more of the following pieces of information, including but not limited to the identity of any drugs within the fluid, the dose of any drugs, the concentration of any drugs, the identity of a diluent, the volume of the fluid wasted, the time and date of the wasting, patient information of the patient for whom the liquid was intended, the drug lot number, the drug maker, and the identity of the waster. This information can be recorded on a computer readable media electrically coupled to processor unit 132, including on an EMR 148, as discussed above.

Figure 6:
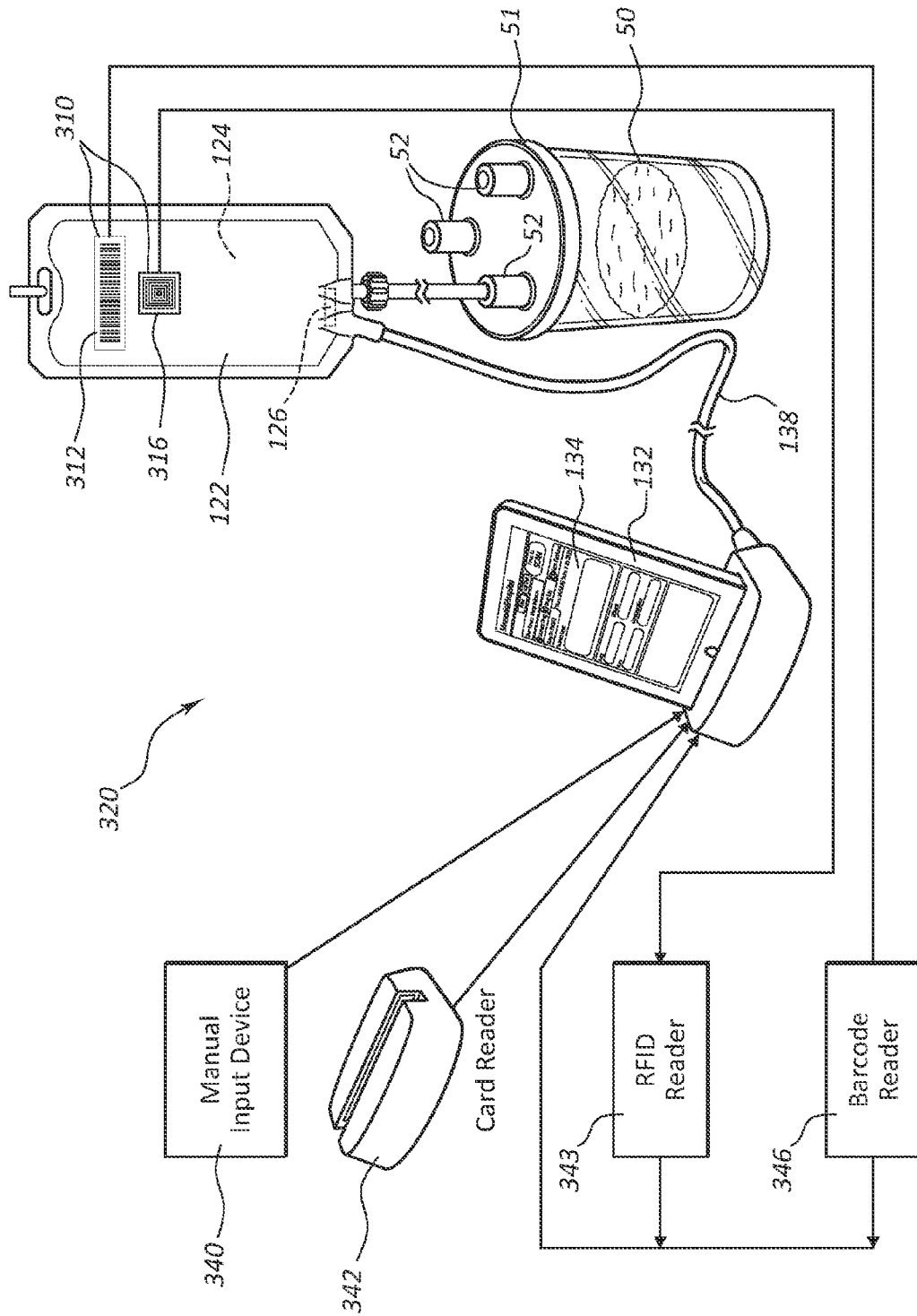
FIG. 6 illustrates a diagrammatic view of a waste disposal system having various inputs in accordance with a representative embodiment of the present invention.

Referring now to FIG. 6, a fluid tracking system 320 is shown. Fluid tracking system 320 includes various input devices coupled thereto configured to provide information to processor unit 132. Through these and other input devices, processor unit 132 receives data relating to the identity of fluid 124 stored in container 122 and a previously determined identity of a fluid 124. Processor unit 132 may further receive information regarding the identity of a patient for whom the fluid was prescribed or intended, the identity of the individual wasting the fluid, the original volume of the fluid placed in container 122, the drug lot number, the drug maker, and other such information. In some embodiments, system 320 comprises a plurality of input devices, such as a manual input device 340 (i.e. a keypad, a mouse, or a touchpad electronically coupled to processor unit 132 for manually entering information), a card reader 342, an RFID reader 343 and a barcode reader 346. Input devices of the present invention may be used to acquire additional information related to the individual wasting the fluid. For example, an input device may be used to acquire the identification of the person wasting the fluid.

Another input device that may be connected to the processor unit 132 is a reader unit for reading information from a container's label. The type of reader unit may be selected based on the nature of a label 310 selected for container 122. For example, a reader unit may include an RFID reader 343 to read information from RFID chips 316 on the label 310, or a barcode reader 346, which can read information from a barcode 312 on the label 310. Accordingly, a label 310 may include various structures configured so that they can be affixed to or printed on container 122. In some instances, label 310 includes text. Label 310 may further include various types of information such as the identity and characteristics of fluid 124 in container 122, the initial volume of fluid 124, a drug lot number, a drug manufacturer, the identity of the pharmacist who prepared the drug, the identity of a drug manufacturer, a drug catalog number, an expiration date of the fluid, and the identity of a patient for whom the fluid 124 is intended. In the various embodiments, some or all of this information may be received by the processor unit 132 and used to identity a fluid being wasted, as explained herein.

Figure 7:
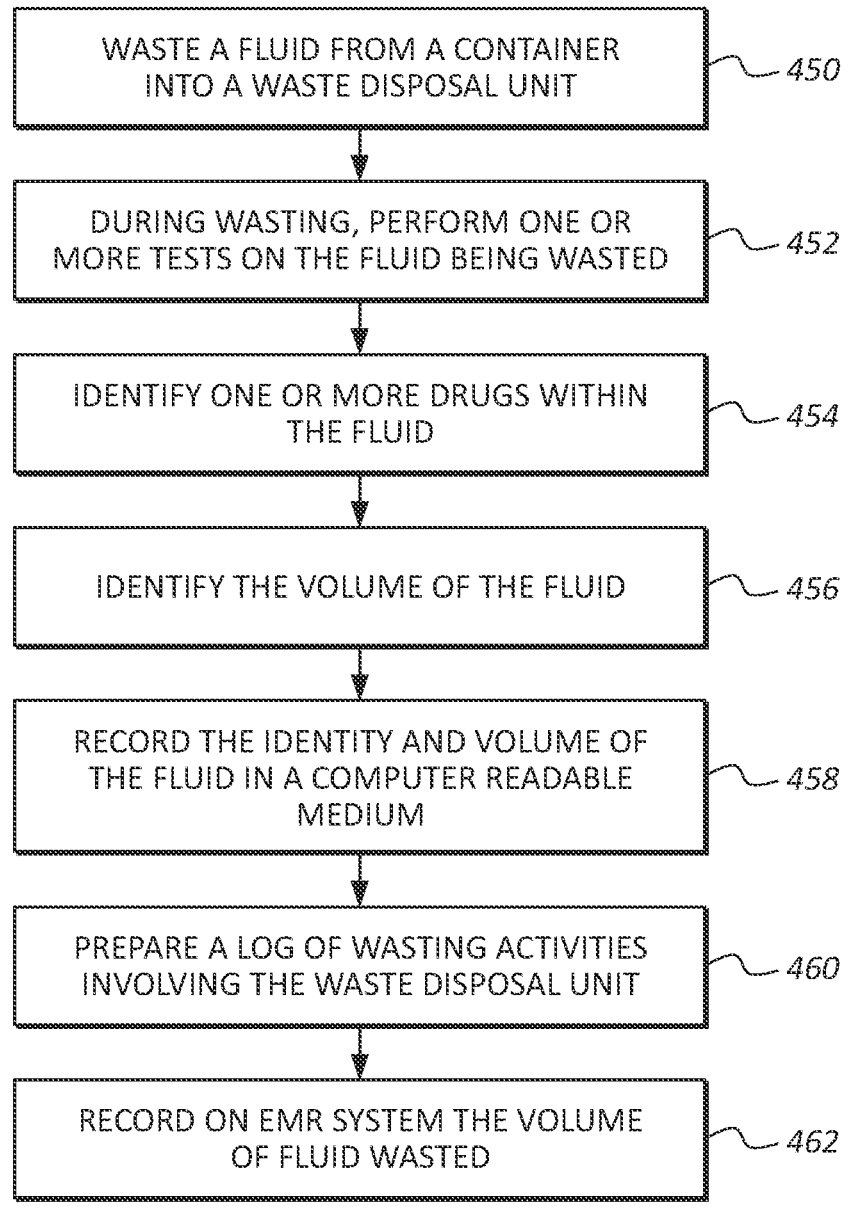
FIG. 7 illustrates a flowchart of a method for using a waste disposal system in accordance with a representative embodiment of the present invention.

Reference will now be made to FIG. 7 which provides a flowchart of a method for monitoring the wasting of fluids. In some embodiments of the present invention, a method is provided having a first step 450 of wasting a fluid from a container into a waste disposal unit. As the fluid is being wasted, a sensor system performs one or more tests on the fluid being wasted into the waste disposal unit (at step 452). Using the sensing measurements, a processor unit of the system identifies one or more drugs within the fluid (at step 454). In addition to identifying the one or more drugs within the fluid, the sensor system identifies the volume of the wasted IV fluid (at step 456). After acquiring information about the container (i.e. the identity of the fluid, the contents of the fluid, the identity of the individual wasting the fluid, and/or other information), the fluid wasting system records this information in a computer readable medium (at step 458). In some embodiments, the fluid wasting system is configured to record this information in a log (or report) that records the information regarding the fluid wasting event (at step 460). In addition to preparing a log or report, the fluid wasting system may further record the amount of fluid wasted in the EMR of the patient for whom the IV fluid was prepared (at step 462).

Figure 8:
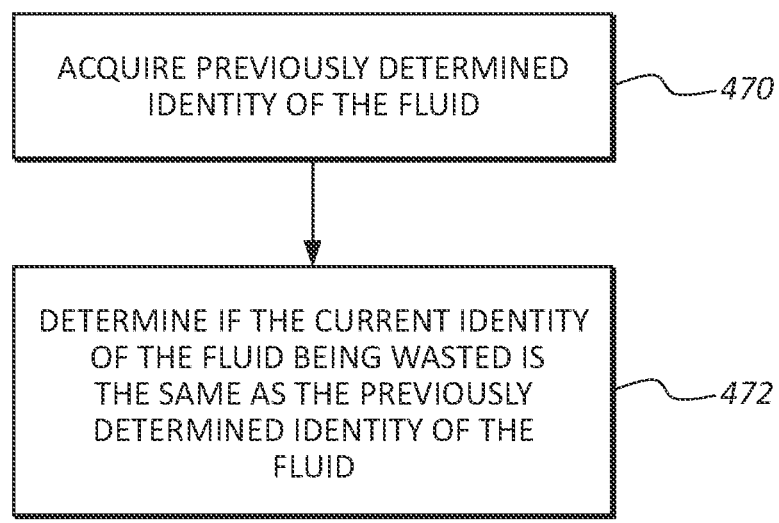
FIG. 8 illustrates a flowchart of a method for auditing the content of a container of fluid in accordance with a representative embodiment of the present invention.

With reference to FIG. 8, a method for auditing the contents of fluid wasted is shown. In some embodiments, a fluid wasting system accesses and acquires a previously determined identity of a fluid in a container (at step 470). The contents information can include the identity of one or more drugs within the fluid, the concentration of one or more drugs within the fluid, and/or the diluent of the fluid. In some embodiments, the identity of a fluid in a container is determined from a record of the fluid identity as contained in an electronic medical record. In other embodiments, the identity of a fluid in a container is determined from information included on a label of the container.

For example, when a physician prescribes a fluid for a patient, the physician may enter the identity, concentration, dose or other parameters or characteristics of the fluid as may be necessary to enable preparation of the fluid by a pharmacist or other technician. In some embodiments, this information is stored in an electronic medical record. In other embodiments, this information is printed onto a label which is applied to the container holding the fluid. Further still, in some embodiments this information is printed onto a label which is adhered to an outer surface of a container, or embedded within the wall of a container holding the fluid. As previously discussed, a label may include a barcode, an RFID chip, or some other form of machine recognizable code that may be scanned or accessed by a processor unit operably coupled to a sensor of the fluid wasting system or the container. For example, an RFID chip may be embedded into the wall of a container, such as a syringe.

A fluid wasting system in accordance with the present invention may access the recorded identity or other characteristic of the fluid. Where the information is stored in an electronic medical record, the fluid wasting system accesses the information from the electronic medical record via a processor unit operably coupled to the fluid wasting system and a network. Where the information is stored in a label, the fluid wasting system accesses the information by scanning the machine recognizable code with a processor unit and/or an input device operably coupled to the processor unit, as discussed above. A sensor and/or sensing elements of the fluid wasting system may then determine the current identity of the fluid being wasted.

After acquiring this information, a processor unit or other computer system compares the current identity of the fluid being wasted with the previously determined identity of the fluid. The system then makes a determination as to whether there has been a change in the identity of the contents of the container (at step 472). If a difference is detected, the wasting system can flag the wasting event as potentially involving a drug diversion.

In some embodiments, a comparison between the previously determined volume of the fluid and the current volume of the fluid being wasted is used to calculate the actual amount of fluid the patient receives for billing purposes. In other embodiments, a comparison between the previously determined volume of the fluid and the current volume of the fluid being wasted is used to calculate and maintain an inventory of the fluid in a storeroom or pharmacy. Further, in some embodiments a comparison between the total medication prepared and the amount of medication administered and "wasted" may be used to form a map of pharmaceutical usage efficiency. This map may then be used to identify areas of improvement and cost savings.

The systems and methods described herein and may further be useful in assisting a clinician and/or pharmacist to accurately verify the identity of the drug at the point of wasting or re-dispensing. Additionally, the fluid wasting system may document the wasting data for reporting purposes or as a requirement for an auditing procedure. The systems and methods of the present invention may also assist a care facility in tracking and auditing wasting activity to determine if fluids are being diverted from the facility. Thus the fluid identification and fluid wasting can provide numerous benefits to care facilities.

The present invention may be embodied in other specific forms without departing from its structures, methods, or other essential characteristics as broadly described herein and claimed hereinafter. The described embodiments are to be considered in all respects only as illustrative, and not restrictive. The scope of the invention is, therefore, indicated by the appended claims, rather than by the foregoing description. All changes that come within the meaning and range of equivalency of the claims are to be embraced within their scope.

The invention claimed is:

1. A system for tracking the disposal of a fluid, the system comprising:
a waste disposal unit having a port defining an inlet to a fluid pathway of the waste disposal unit, the port being configured to allow a fluid container to be coupled to the waste disposal unit to cause fluid within the fluid container to flow through the fluid pathway, the waste disposal unit comprising one or more sensors positioned in the fluid pathway for generating raw data defining one or more characteristics of a fluid as the fluid flows through the fluid pathway; and
a processor unit configured to receive the raw data from the one or more sensors and process the raw data to identify a drug contained in the fluid.

2. The system of claim 1, wherein the one or more characteristics of the fluid comprise one or more of a refractive index, electrochemical potential, impedance, admittance, or conductivity of the fluid.

3. The system of claim 1, further comprising an electronic record operably connected to the processor unit via a network.

4. The system of claim 3, wherein the processor unit is configured to record the identified drug to the electronic record.

5. The system of claim 1, wherein the processor unit is further configured to process the raw data to identify one or more of a diluent of the fluid or a concentration of the drug within the fluid.

6. The system of claim 5, wherein the processor unit is configured to record the identified drug and the one or more of the diluent of the fluid or the concentration of the drug within the fluid to the electronic record.

7. The system of claim 6, wherein the fluid comprises a fluid that was prepared for administration to a patient, and wherein the processor unit is configured to access information previously stored on the electronic record, the previously stored information defining one or more of a drug, diluent, or concentration of the drug within the fluid when the fluid was prepared for administration.

8. The system of claim 7, wherein the processor unit is configured to compare the previously stored information to the identified drug and the one or more of the diluent of the fluid or the concentration of the drug within the fluid.

9. The system of claim 1, wherein the one or more sensors are further configured to identify a volume of the fluid.

10. The system of claim 1, further comprising an input device configured to receive information from a label on the fluid container.

11. The system of claim 1, further comprising a display device operably coupled to the processor unit.

12. The system of claim 1, wherein the fluid pathway further includes one or more of:
- an internal reservoir within the waste disposal unit in which the fluid is collected; or
- an outlet for wasting the fluid into a drain.

13. A system for tracking the disposal of a fluid, the system comprising:
- a waste disposal unit having an internal reservoir for collecting a fluid, the waste disposal unit having a port defining an inlet to the internal reservoir, the port being configured to allow a fluid container to be coupled to the waste disposal unit to cause fluid within the fluid container to flow into the internal reservoir, the waste disposal unit comprising one or more sensors positioned within the port for generating raw data defining one or more characteristics of a fluid as the fluid flows through the port; and
- a processor unit configured to receive the raw data from the one or more sensors and process the raw data to identify a drug contained in the fluid.

14. The system of claim 13, wherein the one or more characteristics of the fluid comprise one or more of a refractive index, electrochemical potential, impedance, admittance, or conductivity of the fluid.

15. A system for tracking the disposal of a fluid, the system comprising:
- a waste disposal unit having a port defining an inlet to a tube that extends through the waste disposal unit, the port being configured to allow a fluid container to be coupled to the waste disposal unit to cause fluid within the fluid container to flow through the tube, the waste disposal unit further including an opening through which the tube passes to allow an end of the tube to be positioned in a drain, the waste disposal unit comprising one or more sensors positioned in the tube for generating raw data defining one or more characteristics of a fluid as the fluid flows through the tube; and
- a processor unit configured to receive the raw data from the one or more sensors and process the raw data to identify a drug contained in the fluid.

16. The system of claim 15, wherein the one or more characteristics of the fluid comprise one or more of a refractive index, electrochemical potential, impedance, admittance, or conductivity of the fluid.

* * * * *